United States Patent [19]

Braden

[11] Patent Number: 5,057,222

[45] Date of Patent: Oct. 15, 1991

[54] PURIFICATION OF PCNB BY SOLVENT EXTRACTION

[75] Inventor: Gary A. Braden, Los Alamitos, Calif.

[73] Assignee: Amvac Chemical Corporation, Los Angeles, Calif.

[21] Appl. No.: 534,895

[22] Filed: Jun. 8, 1990

[51] Int. Cl.⁵ .............................................. B01D 11/04
[52] U.S. Cl. ...................................... 210/634; 210/909
[58] Field of Search ................... 210/634, 909; 203/49

[56] References Cited

U.S. PATENT DOCUMENTS 4,842,696  6/1989  Cazares ................................ 203/409

Primary Examiner—Frank Spear
Attorney, Agent, or Firm—Sughrue, Mion, Zinn Macpeak & Seas

[57] ABSTRACT

Pentachloronitrobenzene (PCNB) is purified by using a liquid-liquid extraction process with polar and nonpolar solvents to remove hexachlorobenzene (HCB). A variety of procedures, solvents and equipment may be employed to carry out the process. A process using a multiplate countercurrent liquid solvent extraction unit, and using DMF and octane as solvents for PCNB and HCB, respectively, is preferred.

17 Claims, 2 Drawing Sheets

BLOCK FLOW DIAGRAM FOR PCNB PURIFICATION

WHERE C IS A MULTIPLATE COLUMN, E IS AN EVAPORATOR AND F IS A FILTER/CENTRIFUGE.

WHERE M IS A MIXER AND S IS A SETTLER

PURIFICATION OF PCNB BY SOLVENT EXTRACTION

FIELD OF THE INVENTION

The present invention relates to a process for purifying pentachloronitrobenzene (PCNB), by a liquid-liquid extraction process which reduces the hexachlorobenzene (HCB) content of the crude PCNB starting material to a concentration which is commercially and environmentally acceptable.

BACKGROUND OF THE INVENTION

Pentachloronitrobenzene is a commercially important fungicide applied to soil and seeds in order to control various plant diseases, specifically those caused by botrytis, fusarium, rhizoctonia and anthracnase.

There are two broad industrial processes for the manufacture of PCNB. The first of these commercial processes is the nitration of pentachlorobenzene with nitric acid in sulfuric acid, as described by Breaux in U.S. Pat. No. 4,026,955. This process has also been described elsewhere, for example, U.S. Pat. Nos. 4,147,732; 4,138,438; and 4,057,590. The other, more important process for the production of PCNB involves chlorination of nitrobenzene in chlorosulfonic acid using iodine as a catalyst, as described, for example, by Thurston in "Fiat Formal Report No. 949". A variation of this process is disclosed by Lojewski in U.S. Pat. No. 3,026,358. Here in an attempt to reduce the final HCB content, chloronitrobenzene is used as the starting material. The PCNB obtained with the two types of prior art commercial processes described above contains HCB in concentrations above 0.1% by weight, even when mild reaction conditions that severely affect productivity are used.

Studies have demonstrated that HCB is an animal carcinogen, making the presence of HCB in fungicides undesirable. As a result, on Apr. 23, 1988 the Office of Pesticides and Toxic Substances of the Environmental Protection Agency set the environmentally acceptable standard level of HCB in PCNB at 0.1% by weight or less. Thus, in order to comply with this standard, commercial manufacturers have had to implement new technologies to reduce the HCB level in PCNB to 0.1% by weight or less.

Several processes for manufacturing PCNB having a reduced HCB content have been patented in recent years. These processes included the conversion of HCB to PCNB using pentaclorothiophenol (U.S. Pat. Nos. 4,454,362 and 4,461,918) and using pentachlorobenzonitrile (U.S. Pat. No. 3,984,487). These two routes represent significant advances in the production of relatively pure PCNB, however they have the disadvantage of using HCB as a starting material.

Another method for removing HCB from PCNB involves distillation, as described by Cazares in U.S. Pat. No. 4,842,696. This process has the disadvantage of requiring that the PCNB be melted prior to distillation and requires high temperatures and/or reduced pressures to effect the distillation. Due to the high temperatures, it is particularly critical that the crude PCNB have no basic impurities present in order to prevent the formation of dioxins, which are of extreme toxicological concern. This process has the further disadvantage of requiring solidification of the melt of PCNB after removal of the HCB.

SUMMARY OF THE INVENTION

It is an object of this invention to provide a commercially and environmentally acceptable grade PCNB product from the relatively impure PCNB already obtained by conventional processes.

It is another object of this invention to provide a process which, by means of readily available liquid-liquid extraction apparatus, can provide a PCNB product having a commercially and environmentally acceptable concentration of HCB. for example below 0.2% by weight, and preferably below 0.1% by weight.

It is a further object of this invention to provide a process for the purification of PCNB that utilizes energy efficient unit operations to effect that purification and to enable the use of standard conditions.

In accordance with one aspect of the invention, a PCNB product containing commercially and environmentally acceptable amounts of HCB, such as HCB levels below 0.2% by weight and preferably below 0.1% by weight, is prepared by extracting PCNB in a polar and nonpolar solvent system. The PCNB is retained preferentially by the polar solvent, and the HCB is retained preferentially by the nonpolar solvent. The extraction can be conducted in a broad range of equipment arranged in a number of configurations that are well known to those skilled in the art of solvent extraction processes.

DETAILED DESCRIPTION OF THE INVENTION

Figure 1:
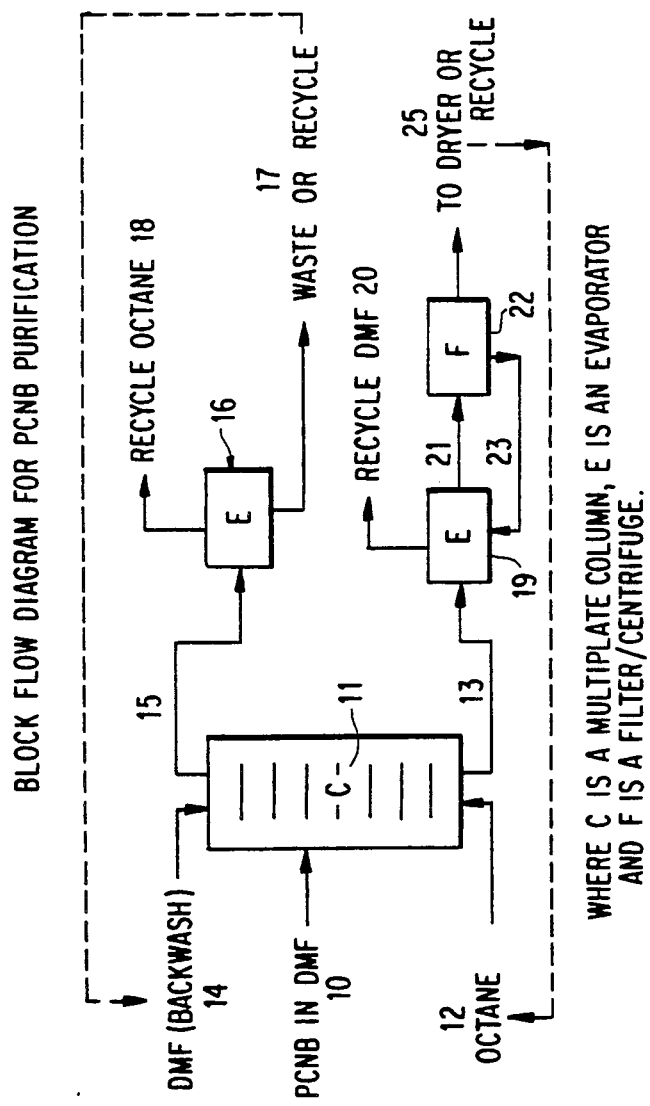
FIG. 1 is a block flow diagram illustrating a possible configuration for a continuous column system of the process. This diagram also illustrates a possible configuration with reflux that allows for increasing the purity and/or yield from the process.

Solvent extraction generically is an excellent manner for purifying a number of materials using an approach of either solids leaching or liquid-liquid extraction. Approaches based on extraction have a number of advantages over distillation processes in that they are conducted at relatively low temperatures, do not require vacuum, are generally energy efficient, and can exhibit a high degree of specificity for the desired purification. Generic parameters for the selection of a solvent or solvent pair have been recognized for a number of years, although it is extremely difficult to determine with any degree of certainty a specific solvent or solvent pair for a particular purification.

The process of this invention may be practiced in a wide variety of equipment known to those skilled in the art of solvent extraction processes. For example, the process may be practiced as either a batch or a continuous process. For either approach, cross current or counter current operational modes may be used, and the PCNB may be added to the process equipment at either an end or to one of the center stages of the equipment. Liquid-liquid extractions are typically run by any of three routes, mixer/settler systems, liquid-liquid extraction tower systems, or centrifugal contacters. The particular equipment used in this process may be any of several types of mixer/settlers, any of several types of column configurations or any of several types of centrifugal contacters. The separation of the two phases may be conventional gravity settling, or by any of several enhanced separators such as enhanced gravity settlers or centrifugal separators.

In selecting the solvents to be used in any of these systems, it is necessary for the solvent pair to have specific properties that allow the separation to be made. For commercial interest, it is necessary that several additional properties be obtained in the solvent pair. Thus, while some general guidelines do exist for the selection of the solvents, in a system involving crude PCNB containing HCB and other impurities, these guidelines are, at best, difficult to apply because these particular compounds have very similar structural properties. It is thus quite unexpected that this purification can be accomplished at all with a liquid-liquid solvent extraction system in which one of the solvents is a polar solvent and the other is a nonpolar solvent.

The selection of the particular polar and nonpolar solvents to be used in this process is limited by two broad parameters: 1) that the two solvents form two immiscible phases in the presence of PCNB and its impurities, especially HCB; and 2) that there is a selectivity of one solvent for PCNB (or for HCB) over that of the other solvent. Selectivity, or the separation factor $\alpha$, is determined by the ratio of the distribution coefficients of the two compounds in the two solvents. The distribution coefficients, usually denoted by D, are the ratio of concentrations of a compound in two immiscible phases when the concentrations in both phases are less than the saturation concentrations for those phases. As used herein selectivity is defined as:

$$\alpha = \frac{[PCNB]_1/[PCNB]_2}{[HCB]_1/[HCB]_2} > 1.0$$

where the square brackets indicate the concentration of PCNB or HCB in solvent 1 and solvent 2 where solvent 1 and 2 are the polar and nonpolar solvents, respectively. As this selectivity value increases, the ease of separation also increases.

The criteria for the immiscibility of the phases are relatively soft criteria as it is not necessary that the solvent pairs be totally immiscible or that the region of heterogeneity be large. Fluid properties are also not critical as long as there exists a temperature at which the selectivity of the solvent pairs can be utilized to effect the separation of the PCNB and HCB enriched process streams.

Polar solvents which may be used for the extraction include, but are not limited to, alcohols, such as ethanol, methanol, and isopropanol; nitrated alkanes, such as nitromethane and nitropropane; sulfonic acids, such as chlorosulfonic acid; amides, such as dimethylformamide and 2-pyrrolidone; acid anhydrides, such as acetic anhydride; substituted $SO_2$ or $SO_3$, such as dimethylsulfoxide; carboxylic acids, such as acetic acid; nitriles, such as acetonitrile; and aromatic amines, such as o-toluidine.

Nonpolar solvents which may be used for the extraction include, but are not limited to, aliphatic hydrocarbons containing two or more carbons, and more preferably, in order to facilitate operation at atmospheric pressure, four or more carbons, such as hexane, cyclohexane, octane, decane, dodecane; carbon disulfide; carbon dioxide; chlorinated or fluorinated hydrocarbons such as carbon tetrachloride and higher carbon number fully- and partially-chlorinated or fluorinated compounds: and aromatics such as toluene, xylene and other substituted benzenes.

The crude PCNB starting materials can be prepared by a number of processes. Several possible processes include, but are not limited to, processes where the crude PCNB starting materials are prepared commercially by halogenating either nitrobenzene, or mono-, di-, tri-, or tetrachloronitrobenzene or mixtures thereof; and processes which prepare the PCNB starting materials by first halogenating benzene, or mono-, di-, tri-, or tetrachlorobenzene or mixtures thereof, followed by nitrating the resulting pentachlorobenzene.

The crude PCNB is typically dissolved in the polar solvent and contacted repeatedly with the nonpolar phase to remove the HCB. The reverse procedure, however, with PCNB dissolved in the nonpolar phase and extracted with the polar solvent, leaving the HCB in the nonpolar phase, can also be used. Furthermore, the crude PCNB need not be completely dissolved in the solvent. The PCNB can also be introduced into the process by combining the chosen solvent (polar or nonpolar) with the crude PCNB to form a slurry or suspension. Thus, the crude PCNB can be introduced into the extraction process in a number of physical states, such as a slurry, suspension, or solution.

In the typical method, the crude, impure PCNB is first dissolved in the polar solvent. The temperature can be elevated to aid dissolution and to allow for a higher solids content in solution. The PCNB/polar solvent solution is then contacted repeatedly with portions of nonpolar solvent to remove HCB and some PCNB. This contact can be batchwise, as in a mixer/settler, or continuous, as in an extraction tower. The polar solvent exits the extraction system containing purified PCNB, while the nonpolar solvent exits containing an elevated amount of HCB relative to the PCNB. The nonpolar extract can be back extracted and repeatedly contacted with fresh portions of the polar solvent containing no PCNB to recover some of the PCNB in the nonpolar extract. Similarly, the nonpolar extract can be back extracted and repeatedly contacted with the polar solvent containing a reflux of PCNB solids removed from the nonpolar extract.

Solids from the nonpolar extract can be proportionately fed back into the extraction process with the polar phase. In this manner, the HCB concentration in the polar solvent can be increased, thus increasing the overall yield of the process. Likewise, the PCNB product from the polar extract can be refluxed back into the system with the nonpolar solvent, which increases the concentration of PCNB in the polar extract. The ratios of the three phases are balanced to give the best combination of extraction of HCB from the PCNB and the highest yield of PCNB possible.

The PCNB can be isolated from the polar solvent by a variety of methods known to those skilled in the art, including but not limited to, crystallization, aqueous quench, and removal of the solvent by distillation. This results in a commercially and environmentally acceptable grade of PCNB products containing, for example, below 0.2% HCB by weight, and usually below 0.1% HCB by weight.

Referring now to FIG. 1, in the typical method, although as noted above other methods may be used, the crude PCNB/polar solvent, such as DMF, is fed through conduit 10 to a center plate of a multistage, countercurrent extraction column 11. A stream of nonpolar solvent, such as octane, is fed through conduit 12 to the base of the column 11, the same end of the column from which the purified PCNB/DMF extract is withdrawn through conduit 13.

Either fresh or recycled DMF is fed into the upper end of column 11 through conduit 14. The fresh or recycled DMF solution may be solids free or contain a proportionate amount of the solids recovered from the octane extract, as shown by conduit 17.

The octane extract containing HCB is removed from the top of column 11 through conduit 15.

The octane extract withdrawn through conduit 15 is fed to an evaporator 16 which preferably is a forced circulation vacuum crystallizer 16. Solids withdrawn from evaporator 16 through conduit 17 may be disposed of as waste or a portion may be recycled for dissolving in DMF, as shown by conduit 14. After separation of the solids in the evaporator 16, a stream of recycled octane is withdrawn through conduit 18 and is returned to column 11 through conduit 12.

The purified PCNB/DMF extract withdrawn from column 11 through conduit 13 is passed to evaporator 19 from which DMF and a small amount of octane are recovered through conduit 20. The DMF and octane in the overhead stream in conduit 20 from evaporator 19 are both condensed and separated. The DMF-rich phase is recycled to the extraction column 11 by conduit 14. The octane-rich phase is recycled to column 11 by conduit 12.

The purified, wet PCNB is passed through conduit 21 to filter/centrifuge 22 to separate purified PCNB solids from polar solvent DMF. The recovered DMF is recycled to either evaporator 19 through conduit 23 if the separation in centrifuge 22 is done hot, or to the extraction column 11 through conduit 14, if the separation is done cold.

The DMF wetted, purified PCNB solids are then recovered through conduit 25 and sent to a dryer for drying under reduced pressure to reduce the DMF solvent content to an acceptable concentration. The resulting dried solids are the finished product ready for packaging, shipment and use.

The overhead from the vessel to which the octane-rich stream is fed (solids rich in HCB) contains a small amount of DMF. This condensed stream is also recycled to the extraction area.

Figure 2:
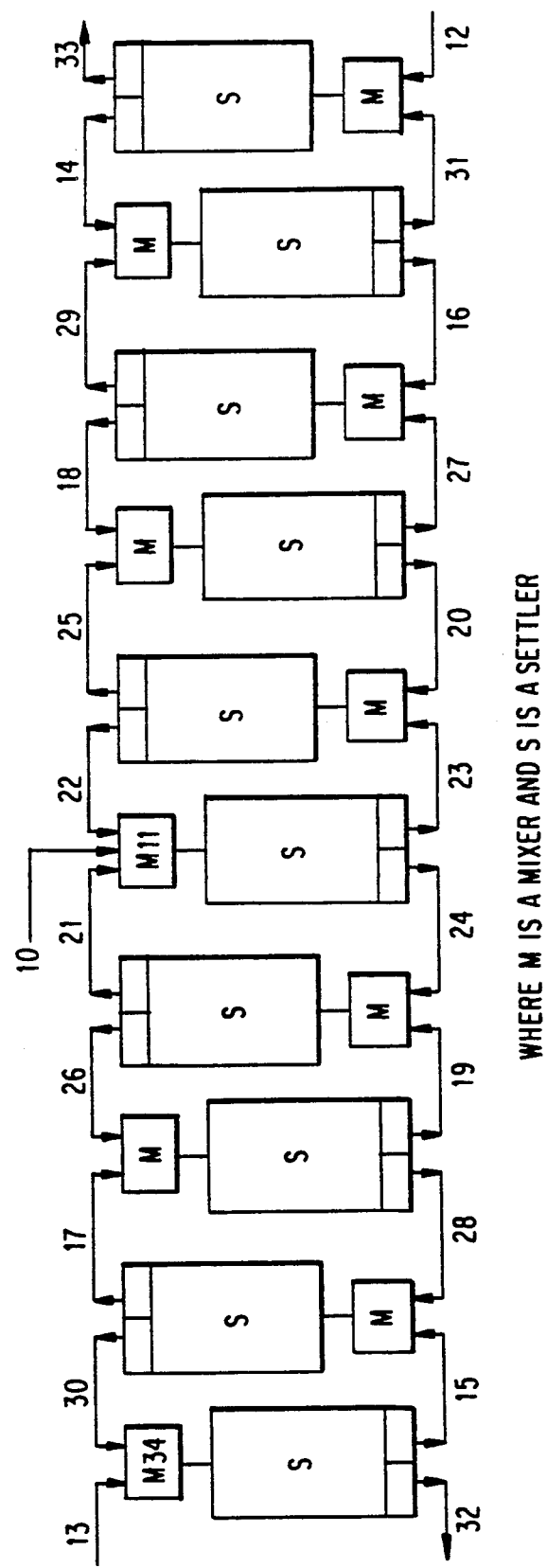
FIG. 2 is a block flow diagram illustrating a possible configuration for a mixer/settler system of the process.

Another equipment configuration for practicing this process is illustrated by FIG. 2, which is a typical equipment configuration for mixer/settlers. The number of stages in this mixer/settler system is for illustration purposes only, as the actual number may be greater or less than those shown, depending on the desired economic objectives of the process. Furthermore, the mixer/settlers in the system may be any of a wide variety of designs that are known to those skilled in the art.

In the typical method, crude PCNB dissolved a polar solvent, such as chlorosulfonic acid (CSA), is introduced into a mixer 11 of one of the central stages of the mixer/settler system by conduit 10. In mixer 11, the PCNB/CSA solution is contacted with both a CSA polar phase, entering through conduit 21, and a nonpolar phase, such as carbon sulfide ($CS_2$), entering through conduit 22.

Fresh $CS_2$ is fed into the system through conduit 12 on the extreme right stage, and flows through the entire system through the even-numbered conduits 14, 16, 18, 20, 22, 24, 26 28, and 30. Fresh CSA is fed into the system through conduit 13 on the extreme left stage, and flows through the entire system through the odd-numbered conduits 15, 17, 19, 21, 23, 25, 27, 29 and 31. The fresh CSA entering mixer 34 through conduit 13 also acts as a back wash of the $CS_2$ extract entering mixer 34 through conduit 30.

The CSA extract containing the PCNB product exits the system through conduit 33, while the HCB-rich $CS_2$ extract exits through conduit 32. These two extract streams are then processed to recover the purified PCNB, the HCB-rich solids from the nonpolar extract, and the extract solvents themselves in any of a number of ways known to those skilled in the art, such as the system illustrated in FIG. 1.

The recovered solvents can be recycled to the mixer/settler system in a manner analogous to that used in FIG. 1, where in this system the nonpolar extract is returned to this system through conduit 12 and the polar through conduit 13. Similarly, there can be reflux of the solids recovered from both the polar and nonpolar extracts as illustrated in FIG. 1, resulting in the same advantages in product yield and/or concentration.

While the foregoing processes have been described with reference to particular solvent pairs, DMF/octane and chlorosulfonic acid/carbon disulfide, other solvents may be used, such as those previously described. Also, as noted above, the equipment used for this process is normally a differential stage column contacter, but the process can also be conducted in discrete vessels, as for example the mixer/settler system of FIG. 2, simple batch vessels with storage for the intermediate process streams, or in centrifugal contactors.

EXAMPLE 1

A solution of 1.06 gms of crude PCNB having a composition of 1.21% HCB and 95.01% PCNB was dissolved in 102 ml of chlorosulfonic acid (as a polar solvent). This solution was contacted with 100 ml of carbon disulfide as a nonpolar solvent. Contact was done in a shake flask by shaking for at least 15 minutes. The mixture was allowed to settle into two phases; the upper nonpolar phase being 81 ml and the lower polar phase being 119 ml. Solids recovered from the polar phase had 0.2% HCB and 97.86% PCNB whereas the solids recovered from the nonpolar phase had 1.83% HCB and 97.69% PCNB. This illustrates that the solvent pair exhibited selectivity in the extraction of the HCB over the extraction of PCNB.

EXAMPLE 2

In experiments conducted in the same fashion as Example 1, crude PCNB having the same composition as used in Example 1 was dissolved in chlorosulfonic acid and aliquots were contacted with cyclohexane and nonane as nonpolar solvents. Solids recovered from the nonpolar cyclohexane solvent showed 2.84% HCB and 91.78% PCNB and solids recovered from the nonane showed 1.74% HCB and 98.26% PCNB. showing that any nonpolar solvent which forms an immiscible phase in the system of crude PCNB and the polar and nonpolar solvents may be used to effect the purification of the crude PCNB.

EXAMPLE 3

To illustrate that nonpolar solvents of other classes of compounds form immiscible mixtures with chlorosulfonic acid solutions of PCNB. aliquots of the polar chlorosulfonic acid solution of Example 1 were contacted with equal volumes of carbon tetrachloride and with toluene (as nonpolar solvents). In both cases, after thorough mixing, the mixture separated into two phases, polar and nonpolar.

EXAMPLE 4

A solution of 0.94 gms of crude PCNB having a composition of 1.21% HCB and 95.01% PCNB was dissolved in 100 ml of methanol (as a polar solvent). This solution was contacted with 100 ml of cyclohexane as a nonpolar solvent. Contact was done in a shake flask by shaking for at least 15 minutes. The mixture was allowed to settle into two phases; the upper nonpolar phase being 60 ml and the lower polar phase having 140 ml. Solids recovered from the polar phase had 0.6% HCB and 98.6% PCNB whereas the solids recovered from the nonpolar phase had 1.7% HCB and 97.4% PCNB. This illustrates that the solvent pair exhibited selectivity in the extraction of the HCB over the extraction of PCNB.

EXAMPLE 5

A solution of 0.99 gms of crude PCNB having a composition of 1.21% HCB and 95.01% PCNB was dissolved in 100 ml of acetonitrile (as a polar solvent). This solution was contacted with 100 ml of nonane as a nonpolar solvent. Contact was done in a shake flask by shaking for at least 15 minutes. The mixture was allowed to settle into two phases: the upper nonpolar phase being 98 ml and the lower polar phase having 103 ml. Solids recovered from the polar phase had 0.34% HCB and 98.30% PCNB whereas the solids recovered from the nonpolar phase had 1.95% HCB and 94.00% PCNB. This illustrates that the solvent pair exhibited selectivity in extraction of the HCB over the extraction of PCNB.

EXAMPLE 6

Crude PCNB having a composition of 0.76% HCB and 96.40% PCNB was dissolved in 100 ml of dimethylformamide. This solution was contacted with 3 separate 50 ml portions of nonane. The solids recovered from the dimethylformamide phase contained 0.097% HCB. This illustrates that repeated contact of the polar phase with the nonpolar phase will reduce the HCB content to less than 0.1% by weight.

EXAMPLE 7

10.5 gms of crude PCNB having a composition of 0.8% HCB and 98.8% PCNB was dissolved in 45 ml of dimethylformamide (as the polar solvent) at 55° C. This solution was contacted with 45 ml of octane in a mixing cylinder while maintaining the temperature at 55° C. The phases were allowed to separate. The solids isolated from the polar phase contained 0.64% HCB and 99.17% PCNB, while the solids isolated from the nonpolar phase contained 1.51% HCB and 98.49% PCNB. This example demonstrates that the selectivity between the phases can be present at elevated temperatures.

EXAMPLE 8

A solution of 9.5 gms crude PCNB having a composition of 0.48% HCB and 96.21% PCNB in dimethylformamide was pumped into an extraction tower at a midpoint in the tower. Octane was pumped into the extraction tower from the bottom of the tower. A third stream of dimethylformamide was pumped into the extraction tower above the entry point for the PCNB-containing solution. The polar solvent exited from the bottom of the tower, and the nonpolar solvent exited from the top of the tower. Analysis of the two streams showed 90% of the solids were in the polar phase and 10% of the solids were in the nonpolar phase. The composition of the solids in the polar phase contained 0.071% HCB and 96.86% PCNB. while the solids in the nonpolar phase contained 8.37% HCB and 90.47% PCNB. This example demonstrates that selectivity for HCB between the two solvents is maintained when a back extraction with the polar solvent is carried out.

EXAMPLE 9

In experiments conducted in the same fashion as Example 1, crude PCNB having the same composition as used in Example 1 was dissolved in acetic acid and o-toluidine as polar solvents. These solutions were contacted with nonane as a nonpolar solvent. Solids recovered from the nonpolar nonane solvent showed 1.50% HCB and 90.52% PCNB for the acetic acid extraction, and solids recovered from the nonane showed 2.28% HCB and 96.75% PCNB from the o-toluidine extraction. This example demonstrates that other polar solvents which form an immiscible phase in the system of the polar solvent nonpolar solvent and PCNB may be used to effect the purification of the crude PCNB.

While the invention has been described in detail and with reference to specific embodiments thereof it will be apparent to one skilled in the art that various changes and modifications can be made therein without departing from the spirit and scope thereof.

What is claimed is:

1. A process for purifying pentachloronitrobenzene (PCNB) containing HCB as an impurity at concentrations in excess of the commercially and environmentally acceptable level, which comprises the steps of:
   combining the impure PCNB with a polar solvent to form a solution, suspension, or slurry:
   contacting this solution, suspension, or slurry with a second, nonpolar, immiscible solvent to remove HCB;
   recovering a purified PCNB product from the first solvent, wherein the HCB content of said purified PCNB product is below commercially or environmentally acceptable levels.

2. A process for purifying impure pentachloronitrobenzene (PCNB) containing HCB as an impurity in concentrations in excess of the commercially and environmentally acceptable levels, which comprises the steps of:
   combining the impure PCNB with a nonpolar solvent to form a solution, suspension, or slurry:
   contacting this solution, suspension, or slurry with a second, polar, immiscible solvent to remove HCB;
   recovering a purified PCNB product from the second solvent, wherein the HCB content of said purified PCNB product is below commercially or environmentally acceptable levels.

3. The purified PCNB product of claims 1 or 2, wherein the HCB content is 0.2% by weight or less.

4. The purified PCNB product of claims 1 or 2, wherein the HCB content is 0.1% by weight or less.

5. The process of claims 1 or 2, wherein the nonpolar extract is back extracted with fresh polar solvent to recover additional purified PCNB.

6. The process of claims 1 or 2, wherein the extraction is operated on a batchwise basis.

7. The process of claims 1 or 2, wherein the extraction is operated on a continuous basis.

8. The process of claims 1 or 2, wherein the extraction is carried out with dimethylformamide as the polar solvent and octane as the nonpolar solvent.

9. The process of claims 1 or 2, wherein the extraction is carried out with chlorosulfonic acid as the polar solvent and carbon disulfide as the nonpolar solvent.

10. The process of claims 1 or 2, wherein the extraction is carried out with nitromethane as the polar solvent and cyclohexane as the nonpolar solvent.

11. The process of claims 1 or 2, wherein the extraction is carried out with acetic acid as the polar solvent and nonane as the nonpolar solvent.

12. The process of claims 1 or 2, wherein the extraction is carried out with methanol as the polar solvent and nonane as the nonpolar solvent.

13. The process of claims 1 or 2, wherein the extraction is carried out with acetonitrile as the polar solvent and carbon disulfide as the nonpolar solvent.

14. The process of claims 1 or 2, wherein the extraction is carried out at an elevated temperature.

15. The process of claim 14 wherein in the elevated temperature is between 30° C. and 75° C.

16. The process of claims 1 or 2, wherein the extraction product of the nonpolar extract is recycled through the process to increase the HCB content of the polar solvent.

17. The process of claims 1 or 2, wherein the extraction product of the polar extract is recycled through the process to increase the PCNB content of the nonpolar solvent.

* * * * *